(12) United States Patent
Martinez-Ferro et al.

(10) Patent No.: US 10,786,294 B2
(45) Date of Patent: Sep. 29, 2020

(54) ZIP TO THE RIB STERNAL PULL-BACK SYSTEM AND METHOD FOR PECTUS CARINATUM TREATMENT

(71) Applicant: PAMPAMED SRL, Buenos Aires (AR)

(72) Inventors: Marcelo Hernan Martinez-Ferro, Buenos Aires (AR); Gaston Bellia-Munzon, Buenos Aires (AR)

(73) Assignee: PAMPAMED SRL, Buenos Aires (AR)

( * ) Notice: Subject to any disclaimer, the term of this patent is extended or adjusted under 35 U.S.C. 154(b) by 0 days.

(21) Appl. No.: 16/084,731

(22) PCT Filed: Mar. 10, 2017

(86) PCT No.: PCT/EP2017/055718
§ 371 (c)(1),
(2) Date: Sep. 13, 2018

(87) PCT Pub. No.: WO2017/157802
PCT Pub. Date: Sep. 21, 2017

(65) Prior Publication Data
US 2019/0069938 A1    Mar. 7, 2019

Related U.S. Application Data

(60) Provisional application No. 62/308,965, filed on Mar. 16, 2016.

(51) Int. Cl.
*A61B 17/82* (2006.01)
*A61B 17/88* (2006.01)
(Continued)

(52) U.S. Cl.
CPC ........ *A61B 17/823* (2013.01); *A61B 17/8076* (2013.01); *A61B 17/842* (2013.01); *A61B 17/88* (2013.01); *A61B 2017/00526* (2013.01)

(58) Field of Classification Search
CPC .............. A61B 17/56; A61B 2017/564; A61B 17/8061; A61B 17/8076; A61B 17/82; A61B 17/823; A61B 17/842; A61B 17/88
See application file for complete search history.

(56) References Cited

U.S. PATENT DOCUMENTS 4,730,615 A * 3/1988 Sutherland ........... A61B 17/823
24/16 PB
6,024,759 A * 2/2000 Nuss ...................... A61B 17/68
606/237
(Continued)

FOREIGN PATENT DOCUMENTS

| EP | 0238219 | | 9/1987 |
|---|---|---|---|
| RU | 2166292 C1 | * | 5/2001 |
| WO | WO-2015003061 A1 | * | 1/2015 |

OTHER PUBLICATIONS

RU2166292 Machine Translation Retrieved from EPO website on Nov. 13, 2019.*

(Continued)

*Primary Examiner* — Larry E Waggle, Jr.
(74) *Attorney, Agent, or Firm* — Lumen Patent Firm

(57) ABSTRACT

A pectus carinatum sternal pull-back device is provided that includes an implantable subcutaneous chest bar, where a size, a curve, a length and a width of the implantable later chest bar are customized according to predetermined sternum and rib cage dimensions of a pectus carinatum patient, where the customized implantable subcutaneous chest bar includes through holes at the ends of the customized implantable subcutaneous chest bar, and at least a pair of securing straps, where the securing strap includes a channeled head element at a first securing strap end, a semi-ribbed strap, and a curved solid insertion element at a second end, where the channeled head element includes a barb for receiving and locking the semi-ribbed strap, where the (Continued)

securing strap is configured for insertion through the through holes of the implantable subcutaneous chest bar.

7 Claims, 5 Drawing Sheets

(51) Int. Cl.
*A61B 17/80* (2006.01)
*A61B 17/84* (2006.01)
*A61B 17/00* (2006.01)

(56) References Cited

U.S. PATENT DOCUMENTS

| | | | |
|---|---|---|---|
| 7,156,847 B2* | 1/2007 | Abramson | A61B 17/8076 606/60 |
| 7,603,192 B2* | 10/2009 | Martin | A61B 17/8061 700/98 |
| 2004/0117016 A1 | 6/2004 | Abramson | |
| 2014/0257291 A1* | 9/2014 | Houff | A61B 17/8076 606/70 |

OTHER PUBLICATIONS

Abramson et al., "A 5-year experience with a minimally invasive technique for pectus carinatum repair" Journal of Pediatric Surgery (2009) 44, 118-124.

* cited by examiner

ZIP TO THE RIB STERNAL PULL-BACK SYSTEM AND METHOD FOR PECTUS CARINATUM TREATMENT

CROSS-REFERENCE TO RELATED APPLICATIONS

This application is a 371 of PCT application PCT/EP2017/055718 filed on Mar. 10, 2017. PCT application PCT/EP2017/055718 claims the benefit of U.S. Provisional application 62/308,965 filed on Mar. 16, 2016.

FIELD OF THE INVENTION

This invention relates to pectus carinatum treatment. More particularly, the invention relates to minimally invasive surgery for pectus carinatum.

BACKGROUND OF THE INVENTION

Pectus carinatum is a deformity of the chest characterized by a protrusion of the sternum and ribs.

Currently, surgically implanted orthotic braces are used for some cases of pectus carinatum. With the cases of children, teenagers, and young adults that wish to avoid surgery, a chest-wall brace has been used that is configured to apply direct pressure on the protruding area of the chest, where the brace is essential for the success of this treatment approach. In one instance, the brace includes front and back compression plates that are anchored to aluminum bars. These bars are bound together by a tightening mechanism, which varies from brace to brace. This device is easily hidden under clothing and must be worn from 14 to 24 hours a day. The wearing time varies with each brace manufacturer and the managing physicians protocol, which could be based on the severity of the carinatum deformity and if it is symmetric or asymmetric.

In some instances, the brace may be worn on the skin or it may be worn over a body 'sock' or sleeve specifically designed to be worn under braces.

For patients with severe pectus carinatum, surgery may be necessary. Minimally invasive surgery for pectus carinatum (PC) has shown to be an effective surgical procedure, although with current approaches the mayor drawback is implant fixation.

What is needed is a surgical technique and apparatus that uses dedicated custom-made implants and an efficient reduced complexity fixation system.

SUMMARY OF THE INVENTION

To address the needs in the art, a pectus carinatum sternal pull-back device is provided that includes an implantable subcutaneous chest bar, where a size, a curve, a length and a width of the implantable subcutaneous chest bar are customized according to predetermined sternum and rib cage dimensions of a pectus carinatum patient, where the customized implantable subcutaneous chest bar includes through holes at the ends of the customized implantable subcutaneous chest bar, and at least a pair of securing straps, where the securing strap includes a channeled head element at a first securing strap end, a semi-ribbed strap, and a curved solid insertion element at a second end, where the channeled head element includes a barb for receiving and locking the semi-ribbed strap, where the securing strap is configured for insertion through the through holes of the implantable subcutaneous chest bar.

According to one aspect of the invention, the implantable subcutaneous chest bar includes material selected such as titanium, or surgical steel.

In another aspect of the invention, the predetermined sternum and rib cage dimensions include a 3D digital image of the sternum and rib cage dimensions from a patient according to output from a CT scan of the patient. Here, a 3D plastic printed test bar is configured from the 3D digital image of the sternum and rib cage dimensions for test fitting the implantable subcutaneous chest bar.

In a further aspect of the invention, the through holes include oval through holes or elongated through holes, where the through holes are a pattern of the through holes, where the pattern is configured to direct tension forces exerted on the through holes in a splayed direction from the pattern of through holes.

In yet another aspect of the invention, the semi-ribbed strap includes a narrowed material region that is proximal to a middle of the semi-ribbed strap, where the semi-ribbed strap is ribbed along a span from proximal to the channeled head to proximal to the narrowed material region and is un-ribbed from proximal to the narrowed material region to the curved solid insertion element.

According to a further aspect of the invention, the securing strap has the strap portion made of a polymer plastic and the curved solid insertion element includes a material such as stainless steel.

According to one embodiment of the invention, a method of pectus carinatum sternal pull-back is provided that includes marking bar entry and exit sites on a patient rib cage, selecting intercostal spaces on the patient rib cage, making bilateral skin incisions at the selected intercostal spaces, creating a submuscular tunnel from an anterior aspect of the bilateral incisions to a highest point of a pectus carinatum sternal defect, advancing a subcutaneous dissector into the submuscular tunnel from a proximal side of the rib cage to a distal side of the rib cage, pulling a customized implantable subcutaneous chest bar, using an umbilical tape, through the submuscular tunnel to a predetermined position on the rib cage, placing securing straps around selected ribs of the rib cage, where the selected ribs are located on each side of the rib cage, where the securing straps are passed through eyelets of the customized implantable subcutaneous chest bar, applying a pressure to the anterior chest wall while tightening the securing straps for correcting the pectus carinatum sternal defect, and closing the bilateral skin incisions.

DETAILED DESCRIPTION

Experience accumulated with non-surgical treatment by means of dynamic compression, providing a better understanding of the mechanics of the thoracic chest in pectus carinatum patients. The present invention provides a new surgical technique using dedicated custom-made implants and a new fixation system.

Before surgery, a test corrective bar is designed using digital 3D design software to output a plastic 3D printed test bar of the subcutaneous bar to be later implanted, where the process starts with 3D software processing of the patient's CT scan to produce a 3D digital image of the rib cage of the pectus carinatum patient. The 3D digital image is used to print a 3D plastic test bar that is used to fit the customized implantable subcutaneous chest bar in the patient and check if the design, size, curve, length and width of the bar is correct when placed exactly at the level of the thorax where the real and final implant made out of metal (surgical steel or titanium depending on the patient's need) will be placed. A clinic template fitting session to the patient is scheduled prior to surgery prior to the final manufacture of a personalized metal bar implant.

In one embodiment of the invention, a pectus carinatum sternal pull-back device is provided that includes an implantable subcutaneous chest bar, where a size, a curve, a length and a width of the implantable later chest bar are customized according to predetermined sternum and rib cage dimensions of a pectus carinatum patient, where the customized implantable subcutaneous chest bar includes through holes at the ends of the customized implantable subcutaneous chest bar, and at least a pair of securing straps, where the securing strap includes a channeled head element at a first securing strap end, a semi-ribbed strap, and a curved solid insertion element at a second end, where the channeled head element includes a barb for receiving and locking the semi-ribbed strap, where the securing strap is configured for insertion through the through holes of the implantable subcutaneous chest bar.

Figure 1A:
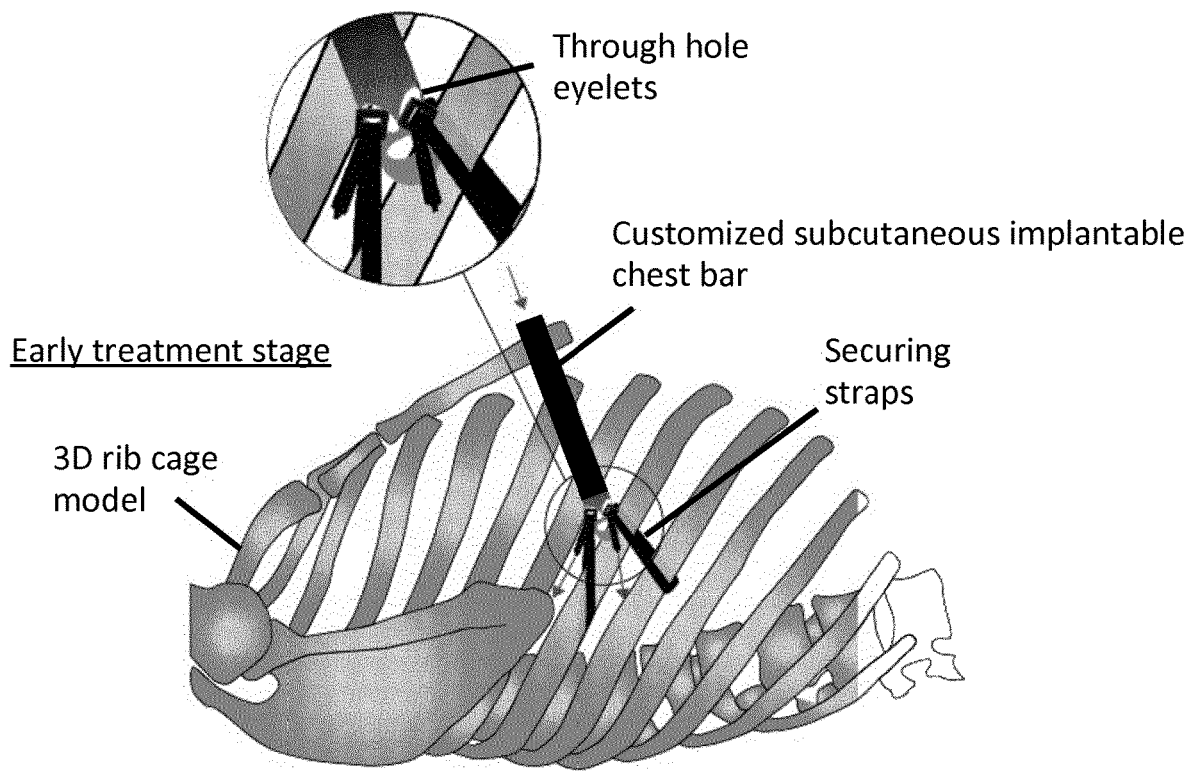
FIGS. 1A-1C show drawings of a pectus carinatum sternal pull-back device being implemented to a patient, according to one embodiment of the invention.
Figure 1B:
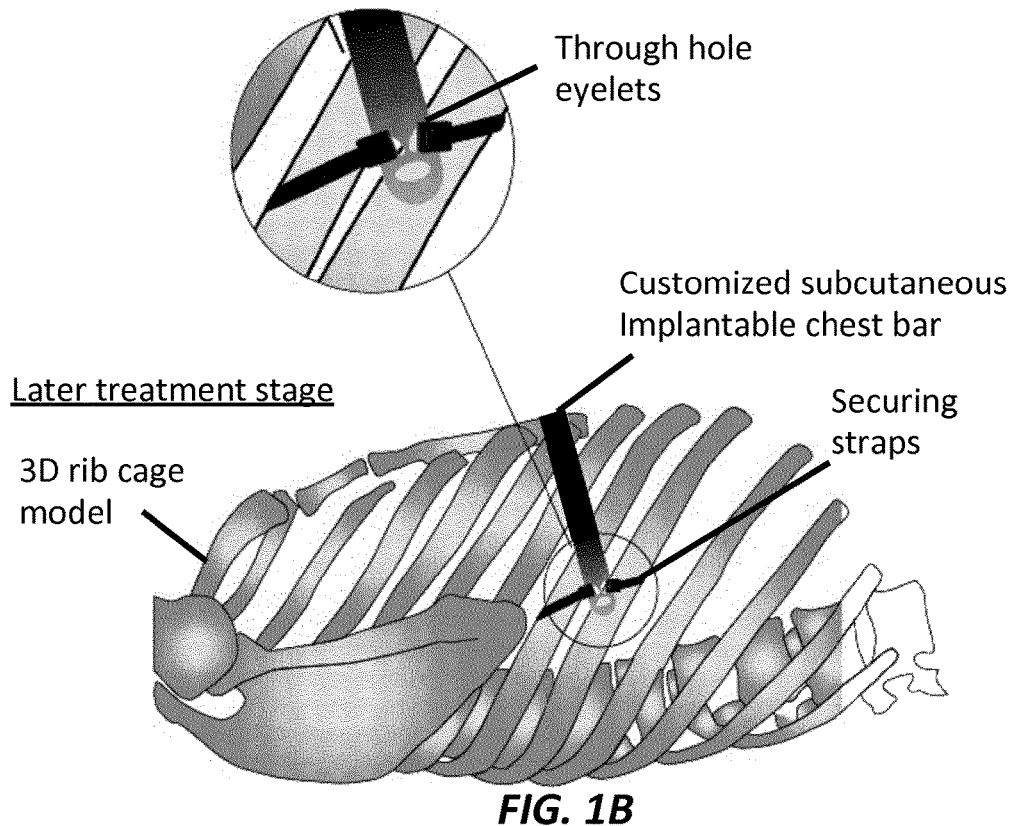
Figure 1C:
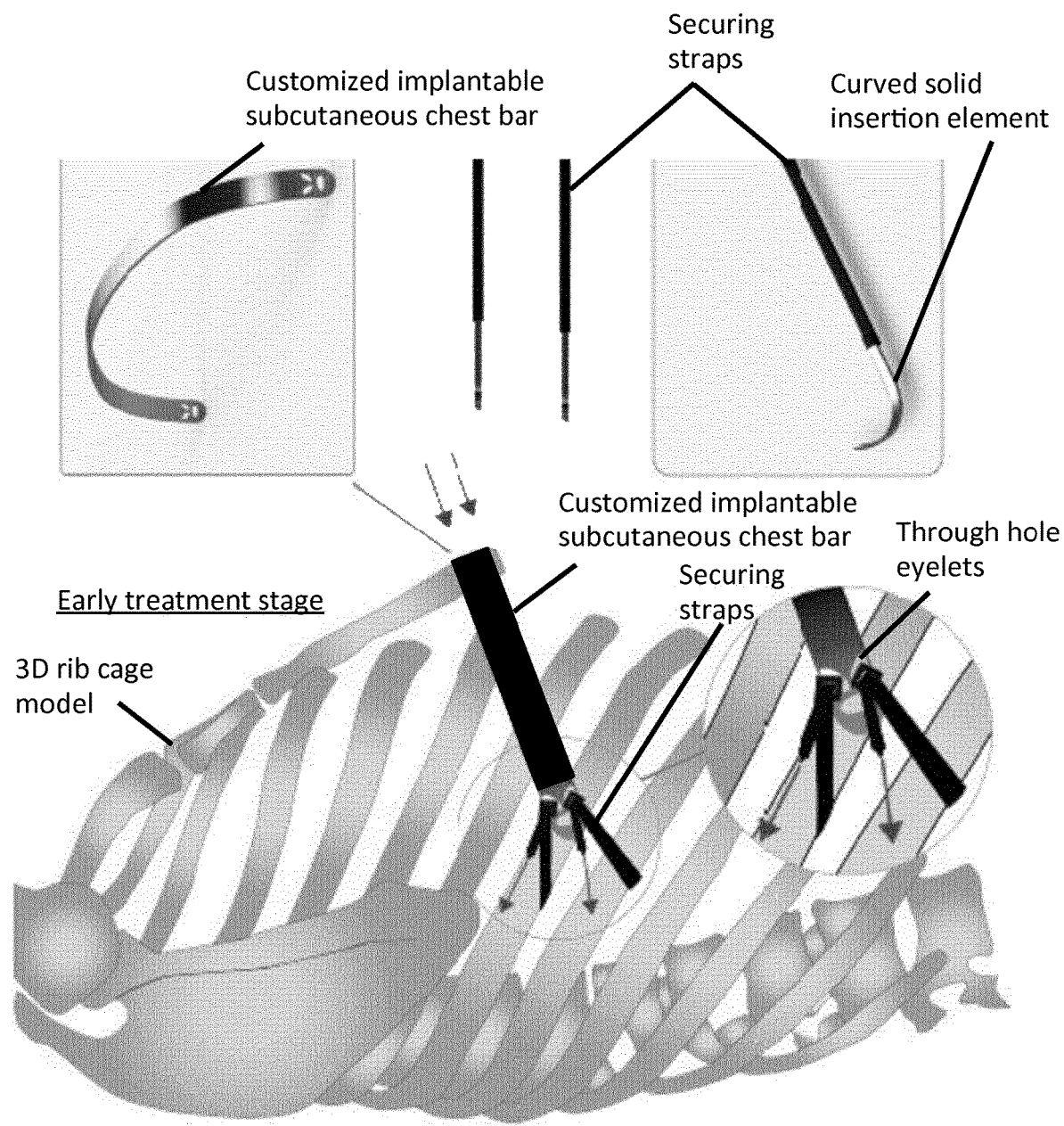

FIGS. 1A-1C show drawings of a customized pectus carinatum sternal pull-back device (implantable subcutaneous chest bar) being implemented to a patient, according to one embodiment of the invention.

In another aspect of the invention, the predetermined sternum and rib cage dimensions include a 3D digital image of the sternum and rib cage dimensions from a patient according to output from a CT scan of the patient. Here, a 3D plastic printed test bar is configured from the 3D digital image of the sternum and rib cage dimensions for test fitting the implantable subcutaneous chest bar (see FIG. 2A).

Figure 2A:
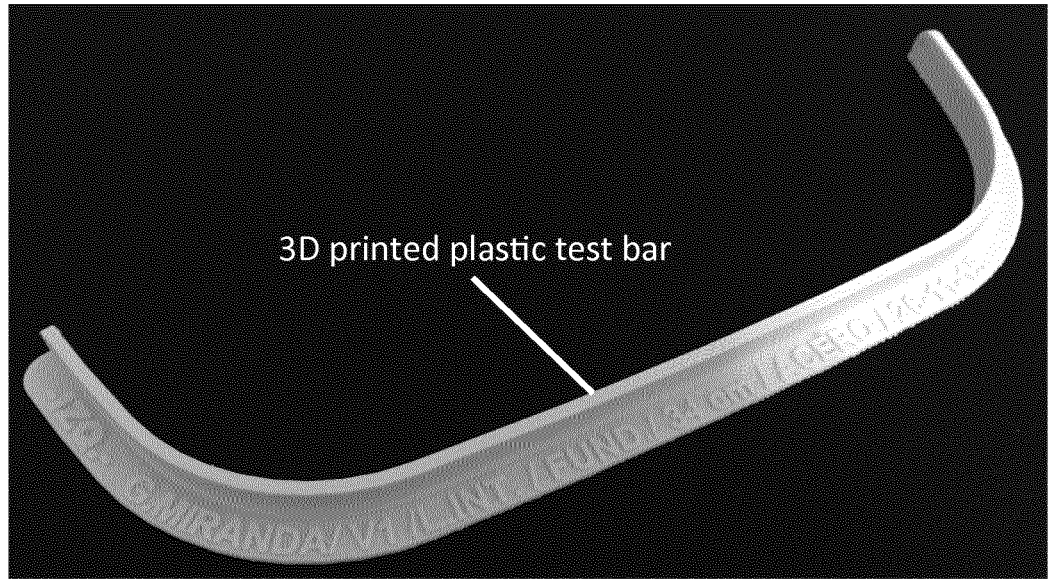
FIGS. 2A-2B show (2A) a 3D printed plastic test bar, and (2B) a customized pectus carinatum sternal pull-back bar (implantable subcutaneous chest bar), according to one embodiment of the invention.
Figure 2B:
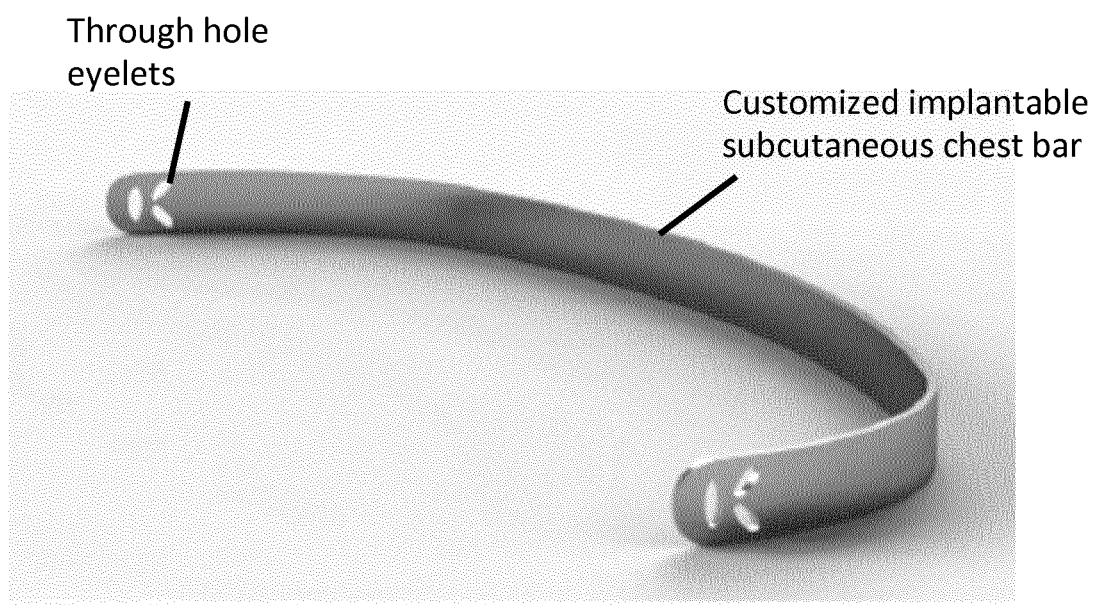
Figures 3A, 3B:
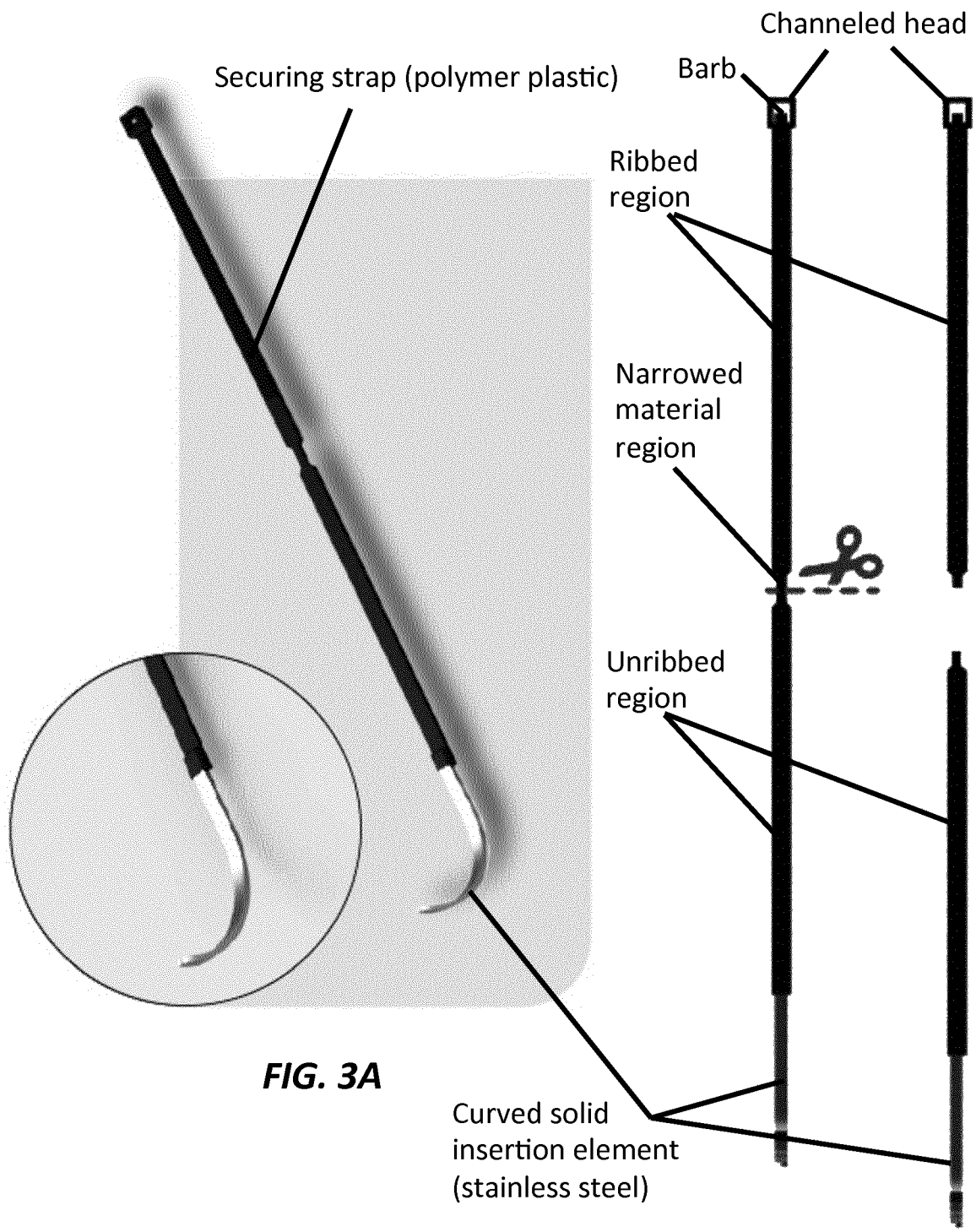
FIGS. 3A-3E show pectus carinatum sternal pull-back securing straps, according to one embodiment of the invention.
Figure 3C:
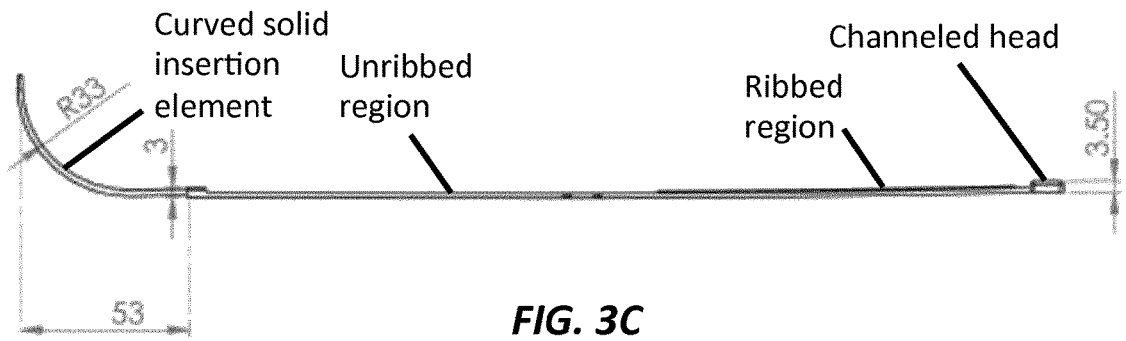
Figure 3D:
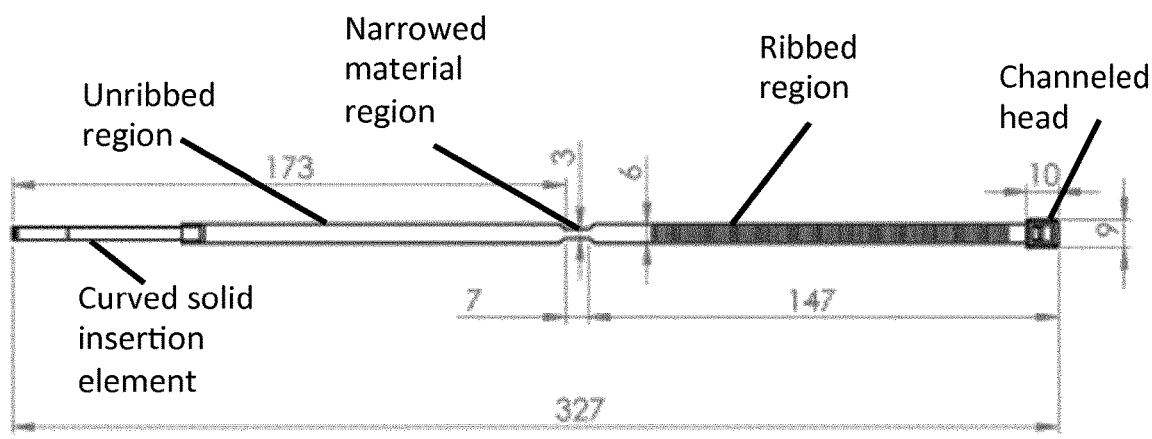
Figure 3E:
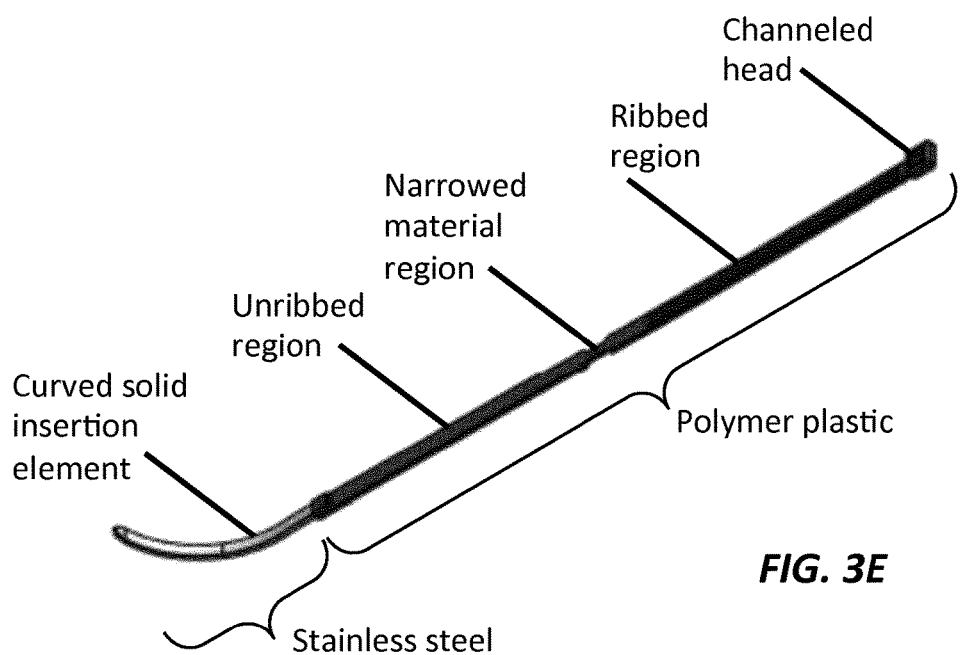

In a further aspect of the invention, the through holes include oval through holes or elongated through holes, where the through holes are a pattern of the through holes, where the pattern is configured to direct tension forces exerted on the through holes in a splayed direction from the pattern of through holes (see FIG. 2B). FIGS. 2A-2B shown a 3D printed plastic test bar and the customized subcutaneous chest bar having the associated eyelet through holes, respectively, according to one embodiment of the invention.

In yet another aspect of the invention, the semi-ribbed strap includes a narrowed material region that is proximal to a middle of the semi-ribbed strap, where the semi-ribbed strap is ribbed along a span from proximal to the channeled head to proximal to the narrowed material region and is un-ribbed from proximal to the narrowed material region to the curved solid insertion element. FIGS. 3A-3E show pectus carinatum sternal pull-back securing straps, according to one embodiment of the invention. According to a further aspect of the invention, strap portion is made of a polymer plastic and the curved solid insertion element includes a material such as stainless steel. In implementation, the securing straps are threaded around the ribs and through the through hole eyelets using the curved solid insertion element, then the securing straps are cut at the narrowed material region to allow for insertion of the ribbed portion through the channeled head to interlock with the barb for securing.

According to one embodiment of the invention, a method of pectus carinatum sternal pull-back is provided that includes marking bar entry and exit sites on a patient rib cage, selecting intercostal spaces on the patient rib cage, making bilateral skin incisions at the selected intercostal spaces, creating a submuscular tunnel from an anterior aspect of the bilateral incisions to a highest point of a pectus carinatum sternal defect, advancing a subcutaneous dissector into the submuscular tunnel from a proximal side of the rib cage to a distal side of the rib cage, pulling a customized implantable subcutaneous chest bar, using an umbilical tape, through the submuscular tunnel to a predetermined position on the rib cage, placing securing strap around selected ribs of the rib cage, where the selected ribs are located on each side of the rib cage, where the securing straps are passed through eyelets of the customized bar, applying a pressure to the anterior chest wall while tightening the securing straps for correcting the pectus carinatum sternal defect, and closing the bilateral skin incisions.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:

1. A pectus carinatum sternal pull-back device, comprising:
   a) an implantable subcutaneous chest bar, wherein a size, a curve, a length and a width of said implantable subcutaneous chest bar are customized according to predetermined sternum and rib cage dimensions of a pectus carinatum patient, wherein said customized implantable subcutaneous chest bar comprises at least a pair of through holes at each end of said customized implantable subcutaneous chest bar; and
   b) securing straps for each of the through holes at each of the ends of said customized implantable subcutaneous chest bar, wherein each of said securing straps as a pair at each end is capable of securing said customized implantable subcutaneous chest bar in a splayed pattern to each securing strap securing individual ribs at each end of said customized implantable subcutaneous chest bar, wherein each of said securing straps comprises a polymeric plastic channeled head element at a first securing strap end, a polymeric plastic semi-ribbed strap, and a stainless steel curved solid insertion element at a second end, wherein said channeled head element comprises a barb for receiving and locking said semi-ribbed strap, wherein each of said securing straps is configured for insertion through said through holes of said implantable subcutaneous chest bar.

2. The pectus carinatum sternal pull-back device of claim 1, wherein said implantable subcutaneous chest bar comprises material selected from the group consisting of titanium, and surgical steel.

3. The pectus carinatum sternal pull-back device of claim 1, wherein said predetermined sternum and rib cage dimensions comprise a 3D digital image of said sternum and rib cage dimensions from a patient according to output from a CT scan of said patient.

4. The pectus carinatum sternal pull-back device of claim 3, wherein a 3D plastic printed test bar is configured from said 3D digital image of said sternum and rib cage dimensions.

5. The pectus carinatum sternal pull-back device of claim 1, wherein said at least pair of through holes comprise oval through holes or elongated through holes, wherein said through holes comprise a pattern of said through holes.

6. The pectus carinatum sternal pull-back device of claim 1, wherein said semi-ribbed strap comprises a narrowed material region that is proximal to a middle of said semi-ribbed strap, wherein said semi-ribbed strap is ribbed along a span from proximal to said channeled head element to proximal to said narrowed material region and is un-ribbed from proximal to said narrowed material region to said curved solid insertion element.

7. A method of pectus carinatum sternal pull-back, comprising
   a) marking bar entry and exit sites on a patient rib cage;
   b) selecting intercostal spaces on said patient rib cage;
   c) making bilateral skin incisions at said selected intercostal spaces;
   d) creating a submuscular tunnel from an anterior aspect of said bilateral incisions to a highest point of a pectus carinatum sternal defect;
   e) advancing a subcutaneous dissector into said submuscular tunnel from a proximal side of said rib cage to a distal side of said rib cage;
   f) pulling a customized bar, using an umbilical tape, through said submuscular tunnel to a predetermined position on said rib cage;
   g) placing securing straps around selected ribs of said rib cage as a pair in a splayed pattern direction relative to said customized bar, wherein said selected ribs are located on each side of said rib cage, wherein said securing straps are passed through eyelets of said customized bar, and wherein each of said securing straps comprises a polymeric plastic channeled head element at a first securing strap end, a polymeric plastic semi-ribbed strap, and a stainless steel curved solid insertion element at a second end;
   h) applying a pressure to an anterior chest wall while tightening said securing straps at each end for correcting said pectus carinatum sternal defect; and
   i) closing said bilateral skin incisions.

* * * * *